US011071867B2

(12) United States Patent
Baru et al.

(10) Patent No.: US 11,071,867 B2
(45) Date of Patent: Jul. 27, 2021

(54) CAPACITOR-DISCHARGE COMMUNICATION SCHEME FOR AN IMPLANTABLE MEDICAL SYSTEM

(71) Applicant: BIOTRONIK SE & Co. KG, Berlin (DE)

(72) Inventors: Marcelo Baru, Tualatin, OR (US); Brian M. Taff, Portland, OR (US); Andrew B. Kibler, Lake Oswego, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 98 days.

(21) Appl. No.: 16/690,944

(22) Filed: Nov. 21, 2019

(65) Prior Publication Data

US 2020/0188681 A1    Jun. 18, 2020

Related U.S. Application Data

(60) Provisional application No. 62/780,954, filed on Dec. 18, 2018.

(51) Int. Cl.
*A61N 1/372* (2006.01)
*H02J 7/34* (2006.01)

(52) U.S. Cl.
CPC ..... *A61N 1/37217* (2013.01); *A61N 1/37288* (2013.01); *H02J 7/345* (2013.01)

(58) Field of Classification Search
None
See application file for complete search history.

(56) References Cited

U.S. PATENT DOCUMENTS

| 9,289,612 | B1 | 3/2016 | Sambelashvili et al. |
| 9,522,280 | B2 | 12/2016 | Fishler et al. |
| 2012/0078322 | A1 | 3/2012 | Dal Molin et al. |
| 2014/0222098 | A1* | 8/2014 | Baru ............... A61N 1/37276 607/16 |
| 2015/0335894 | A1 | 11/2015 | Bornzin et al. |
| 2016/0213937 | A1 | 7/2016 | Reinke et al. |
| 2016/0213939 | A1 | 7/2016 | Carney et al. |
| 2016/0279430 | A1* | 9/2016 | Baru ............... A61N 1/3727 |
| 2018/0185653 | A1* | 7/2018 | Baru ............... A61N 1/371 |

* cited by examiner

*Primary Examiner* — Brian T Gedeon
(74) *Attorney, Agent, or Firm* — Buchanan Ingersoll & Rooney PC

(57) ABSTRACT

An implantable medical system for intra-body communication, comprising an implantable first device. The first device comprises a plurality of capacitors and a DC blocking capacitor. The first device is configured to discharge the plurality of capacitors via the DC blocking capacitor in an encoded sequence to generate a signal.

14 Claims, 4 Drawing Sheets

CAPACITOR-DISCHARGE COMMUNICATION SCHEME FOR AN IMPLANTABLE MEDICAL SYSTEM

CROSS-REFERENCE TO RELATED APPLICATIONS

This patent application claims the benefit of co-pending U.S. Provisional Patent Application No. 62/780,954, filed on Dec. 18, 2018, which is hereby incorporated by reference in its entirety.

TECHNICAL FIELD

The present disclosure relates to an implantable medical system.

BACKGROUND

Medical systems, in particular those involving implantable devices, can benefit from intra-body communication for synchronized operation.

Particularly, U.S. Pat. No. 9,522,280 discloses dual implanted leadless pacemakers, one in the right atrium and one in the right ventricle, with conductive communication between them.

Furthermore, U.S. Pat. No. 9,289,612 discloses an implantable medical system, configured to provide atrio-synchronous ventricular pacing, comprising a first leadless pacing device located in the right ventricle with a sensing extension and a second leadless pacing device implanted in the right atrium. This second device can sense intrinsic depolarizations of the atrium and deliver a pacing pulse during the refractory period of the right atrium following a sensed intrinsic depolarization. The first leadless pacing device in the right ventricle is capable of detecting such pacing pulse generated by the second leadless pacing device and deliver a pacing pulse to the right ventricle an atrio-ventricular (AV) delay interval after detecting such pacing pulse from the second leadless pacing device should an intrinsic ventricular depolarization not be detected prior to the expiration of the AV delay.

Furthermore, U.S. Publication No. 2015/0335894 describes a distributed leadless implantable system that comprises first and second leadless implantable medical devices (LIMDs) configured to be implanted entirely within first and second chambers of the heart, wherein each LIMD comprises a housing having a proximal end configured to engage local tissue in a local chamber, electrodes located along the housing and cardiac sensing circuitry configured to detect intrinsic and paced cardiac events occurring in a near field associated with the local chamber.

U.S. Publication No. 2012/0078322 discloses an active implantable medical device having wireless communication of data via electrical pulses conducted by the interstitial tissues of the body. This device includes a pair of electrodes and generates pulse trains consisting of a series of electrical pulses applied to the electrodes. The pulse train is modulated by digital information (data) that is produced by the device. A regulated current or voltage source is used to generate current or voltage pulses to form the pulse train. Each current or voltage pulse is a biphasic pulse comprising a positive and negative alternation. The biphasic current or voltage modulated by the digital information is injected between the electrodes and wirelessly communicated.

U.S. Publication No. 2016/0213939 discloses an implantable cardioverter defibrillator (ICD) configured to transmit a tissue conduction communication (TCC) signal. The ICD includes a TCC transmitter module configured to generate the TCC signal and transmit the TCC signal via a plurality of electrodes. The TCC signal comprises a biphasic signal having an amplitude and a frequency, wherein at least one of the amplitude and the frequency are configured to avoid stimulation of tissue of the patient. The TCC transmitter module comprises protection circuitry coupled between a current source and the plurality of electrodes, wherein the protection circuitry is configured to protect the signal generator from an external anti-tachyarrhythmia shock delivered to the patient.

U.S. Publication No. 2016/0213937 discloses an implantable medical device which comprises a communication module that comprises at least one of a receiver module and a transmitter module. The receiver module is configured to both receive from an antenna and demodulate an RF telemetry signal, and receive from a plurality of electrodes and demodulate a tissue conduction communication (TCC) signal. The transmitter module is configured to modulate and transmit both an RF telemetry signal via the antenna and a TCC signal via the plurality of electrodes. The RF telemetry signal and the TCC signal are both within a predetermined band for RF telemetry communication. In some examples, the IMD comprises a switching module configured to selectively couple one of the plurality of electrodes and the antenna to the receiver module or transmitter module.

When considering techniques for coordinating ventricular pacing with intrinsic depolarization in another chamber of the heart by delivering an electrical pulse in the other chamber and sensing it in the ventricle, as described in U.S. Pat. No. 9,289,612, a drawback may be encountered when a pacing pulse is delivered in the refractory period of the other chamber following a sensed intrinsic depolarization in such chamber and that the pacing pulse is detected by the sensing module of the ventricular leadless pacemaker via the adjustment of its sensitivity only. This would imply that a detection of the pacing pulse utilizes the same frequency bandwidth as for cardiac sensing. This means low frequency and thus a long time constant for balancing the charge introduced in the other chamber by the signaling pacing pulse.

Further, when using implant-to-implant event messaging by conductive communication utilizing a series of individual pulses as, e.g., described in U.S. Pat. No. 9,522,280, which may include, for example, a low frequency pulse followed by a high frequency pulse train, delivered after a sensed event in a chamber it can prove intricate to provide a proper charge balancing of these pulses for the receiver sense amplifier in the other chamber not to pick up artifacts from the communication pulses and confuse them with an intrinsic event in such chamber the receiver implant monitors. Also here, a long time constant may become an issue as described above as the same pulse generator for pacing is utilized for conductive communication. Further, utilizing a conductive high frequency train of pulses with µs on/off bits as described in U.S. Pat. No. 9,522,280 translates into substantial extra power consumption in the right ventricle leadless pacemaker as the communication receiver amplifier of such device may be required to be on up to 80% of the time listening for a possible message that an atrial event occurred.

The present invention is directed at overcoming one or more of the above-mentioned problems.

SUMMARY

Based on the above, it is an objective to provide a low-power intra-body communication scheme suitable for implementation in small implantable devices whose signaling can particularly coincide with any ongoing intrinsic tissue depolarization that may occur.

An implantable medical system for intra-body communication is disclosed comprising at least an implantable first device comprising a plurality of capacitors (e.g., a bank of capacitors), wherein the first device is configured to discharge said capacitors in an encoded sequence to generate a signal for intra-body communication, e.g., for communication with a second implantable device. The capacitors may be connected in series.

In an embodiment, the first device comprises a direct current (DC) blocking capacitor, wherein the first device is configured to discharge said plurality of capacitors in an encoded sequence via said DC blocking capacitor. Particularly, according to an embodiment, the DC blocking capacitor comprises a capacity in the range from 60 nF to 100 nF. Particularly, the DC blocking capacitor can comprise a capacity that amounts to 82 nF.

Particularly, the system enables efficient close-proximity device-to-device communication for use in leadless implantable cardiac rhythm management (CRM) systems. For this, the present invention includes a plurality of capacitors which are discharged in an encoded sequence, resulting in a signal in a reception band of an additional implantable device in the body. Encoded sequence means that the capacitors are discharged in a sequence which delivers information to the receiving unit (e.g., the second implantable device).

Particularly, the system can comprise an implantable second device, wherein the second device is configured to receive said signal and use the information contained or coded therein for performing a function.

According to an embodiment, said second device is a cardiac pacemaker, wherein said function corresponds to delivering an additional pacing pulse to the heart of a patient or inhibiting pacing of a heart of a patient.

Furthermore, according to an embodiment, the first device is configured such that a maximum charge accumulated in each of the capacitors of the plurality of capacitors is sub-threshold to nerve stimulation or cardiac stimulation of a patient when discharged in tissue of the patient.

Particularly, according to a preferred embodiment, the first device is configured to passively charge balance each individual discharge of said sequence of discharges, wherein particularly said sequence is comprised of non-capturing (sub-threshold) discharges for communication.

Further, according to an embodiment, said capacitors of the plurality of capacitors are configured to be charged to a voltage of a battery of the first device or to a reduced voltage generated from the voltage of a battery of the first device.

Further, according to an embodiment, the first device (particularly in case said reduced voltage is used) is configured to charge the plurality of capacitors which may be connected in series and to discharge them in said encoded sequence one at a time in parallel.

Further, according to an embodiment, the first device comprises a control unit configured to manage the plurality of capacitors, wherein particularly the control unit is configured to control charging and/or discharging of the plurality of capacitors, particularly for intra-body communication.

Furthermore, according to an embodiment, the first device comprises a memory, wherein particularly the control unit is connected to the memory.

Further, in an embodiment, the first device comprises a communication unit, wherein particularly the control unit is connected to the communication unit.

Further, according to an embodiment, the communication unit is configured to one of: communicate via said signal due to said discharge of the plurality of capacitors in said encoded sequence; communicate via an inductor of the first device; and communicate in a wireless fashion via an antenna of the first device (i.e., radio communication). Such a communication of the communication unit may be used for programming and/or interrogating the implanted first device using an external programmer. The second device may also incorporate the communication capabilities mentioned above (depending on the therapy application).

Furthermore, according to an embodiment, each capacitor of said plurality (or bank) of capacitors comprises a capacity in the range from 10 nF to 20 nF, particularly 15 nF.

Further, in an embodiment, the first device comprise two electrodes configured for contacting tissue of a patient when the first device is implanted in the patient, wherein the first device is configured to discharge said capacitors in the encoded sequence in tissue of the patient via said electrodes to generate said signal. Particularly, the signal is sub-threshold to nerve stimulation or cardiac stimulation of the patient.

Furthermore, in an embodiment, the first device is configured to discharge said plurality of capacitors in said encoded sequence such that a waveform is created between the two electrodes of the first device in the tissue of the patient, the waveform comprising a plurality of peaks, wherein the respective peak corresponds to a discharge of a capacitor of said plurality of capacitors during said sequence, and wherein each peak is followed by a charge balancing phase, particularly generated by the first device in a passive manner (i.e., autoshort).

Furthermore, the implantable second device of the system (or further implantable devices of the system) is configured to receive said signal via two electrodes of the second device, and to extract the peaks of said waveform and convert the respective peak into a corresponding high digital output.

Further, in an embodiment, the second device comprises a control unit, wherein the control unit of the second device is configured to use a timing between the high digital outputs generated by the second device to determine that an event has been communicated by the first device via said signal.

Furthermore, according to an embodiment, the first device is configured to shift the timing between said peaks so as to communicate information (e.g., to the second device) in addition to the occurrence of said event.

Particularly, the second device can comprise a non-linear pre-processor to extract said signal, and particularly to enhance a difference between the peaks and a noise level.

Furthermore, according to an embodiment, the pre-processor is configured to use an exponential relationship between a gate-source voltage and a drain current of a MOS transistor operating in weak inversion to convert the waveform to a current that is comparable to a threshold. Furthermore, said the non-linear pre-processor can be followed by a current-based comparator for converting the peaks into digital outputs.

Furthermore, according to an alternative embodiment, the non-linear processor consists of or comprises a differentiator and a squaring circuit.

Furthermore, according to an embodiment, a total power consumption of a receiver unit of the second device (or of the first device) configured to receive said signal is lower than 100 nA @ 1.5 V.

Furthermore, according to an embodiment, the first device is a first pacemaker that is configured to be implanted in the right atrium of the patient, and wherein the second device is a second pacemaker that is configured to be implanted in the right ventricle of the patient, wherein particularly the two pacemakers together are configured to operate in the DDD (R) mode (DDD(R): The pacemaker records both atrial and ventricular rates and can pace either chamber when needed, and the pacemaker has a sensor that records a demand for higher cardiac output and can adjust the heart rate accordingly).

Furthermore, according to an embodiment, one of the first and the second device (e.g., the first device) is an intracardiac pacemaker (e.g., a leadless pacemaker) and the other device (e.g., the second device) is an implantable loop recorder configured to monitor at least one physiological signal of a patient, such as e.g. an electrocardiogram (ECG), wherein particularly the loop recorder is configured to communicate via wireless radio communication (e.g., according to a Bluetooth standard) with an external device.

Furthermore, according to an embodiment, one of the first and the second device (e.g., the first device) is an intracardiac pacemaker (e.g., a leadless pacemaker) and the other device (e.g., the second device) is an implantable cardioverter-defibrillator (ICD).

Furthermore, according to an embodiment, the first device is configured to discharge said plurality of capacitors in said encoded sequence into a communication element of the first device.

Particularly, the communication element can be a coil that is configured to emit a magnetic field forming said signal in response to discharging said plurality of capacitors in said encoded sequence into the coil, and wherein, according to an embodiment, the second device comprises a coil configured to detect said signal.

Alternatively, the communication element can be a piezoelectric element that is configured to emit a pressure wave forming said signal in response to discharging said plurality of capacitors in said encoded sequence into the piezoelectric element. In an embodiment, the second device comprises a piezoelectric detector configured to detect said signal.

Additional features, aspects, objects, advantages, and possible applications of the present invention will become apparent from a study of the exemplary embodiments and examples described below, in combination with the Figures, and the appended claims.

DESCRIPTION OF THE DRAWINGS

Other advantages and expedient features of the present invention follow from the following description of sample embodiments, which make reference to the Figures. The Figures are as follows.

DETAILED DESCRIPTION

Particularly, the present disclosure provides a communication scheme utilizing passively-charge-balanced, non-capturing capacitive discharges that permits at least two implantable devices 2, 3 to communicate with each other. A bank of capacitors 102, charged to the implantable first device's 2 battery 104 voltage or a reduced voltage generated from it, are preferably discharged in tissue in an encoded sequence. The receiving second device 3 may utilize a non-linear amplifier to extract the message (see e.g., below). Advantageously, the communication generated according to the various embodiments is low-power and due to the low-value of capacitors required, is suitable for implementation using silicon-integrated passive technology.

Particularly, the present disclosure allows efficient close-proximity device-to-device communication, particularly for use with implantable leadless pacemakers or loop recorders that do not comprise flexible electrode leads extending from a housing Instead, leadless pacemakers have a pacing electrode configured to deliver pacing pulses to the patient, wherein the pacing electrode is arranged on the housing. Particularly, such pacemakers are configured to be implanted into an atrium or ventricle of the patient.

Figure 1:
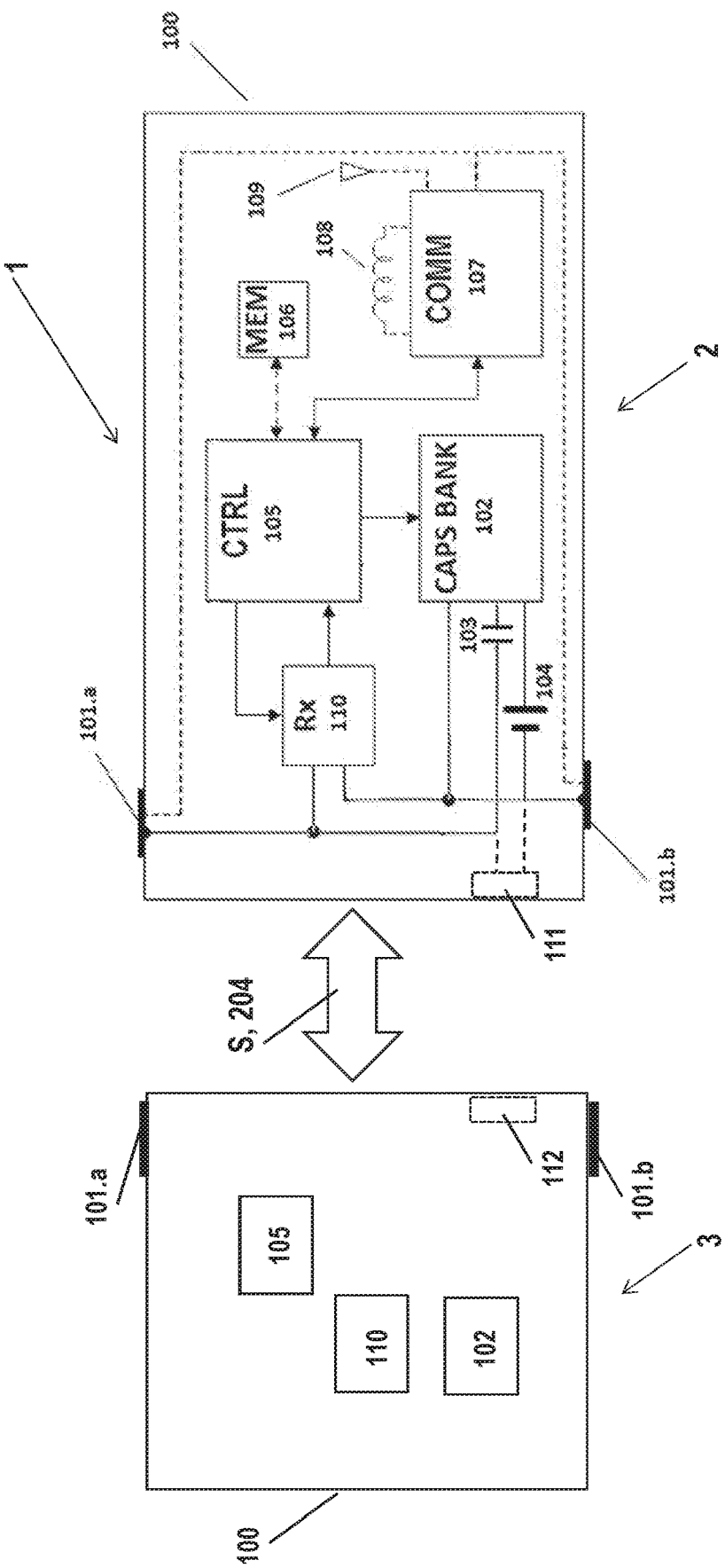
FIG. 1 shows a schematic illustration of an embodiment of an implantable medical system.

Particularly, as shown in FIG. 1, the implantable medical system 1 according to an embodiment comprises at least a first and a second implantable device 2, 3 and includes a plurality of capacitors (e.g., a bank of capacitors, wherein the capacitors are connected in series) 102 which are discharged in an encoded sequence, resulting in a signal S in a reception band of the second device (or several additional devices) 3 in the body of the patient. The second device 3 (or additional devices) preferably uses the information in the encoded capacitive-discharge communication to perform functions which may include delivering additional pacing pulses or inhibiting pacing.

A block diagram of a module 100 of the first device 2, comprising a galvanic-coupling communication scheme, is shown in FIG. 1 on the right hand side. Via at least two electrodes 101.a, 101.b, with electrical contact to living tissue of the patient, the first device 2 discharges a bank of capacitors (CAPS BANK) 102, via a DC blocking capacitor 103, that were previously charged to a voltage of a battery 104 of the first device 2 (e.g., 3.6 V maximum, which also powers the rest of the module 100) or to a lower voltage generated from such battery 104. In the latter case, a preferred approach is to charge the capacitors 102 in series and discharge them one at a time in parallel. In this way, each may have a ratio of the battery 104 voltage (e.g., ½, ⅓, ¼, etc.).

Particularly, module 100 of the first device 2 comprises a control unit (CTRL) 105 that is configured to manage the plurality of capacitors 102. The control unit 105 may be further connected to a memory (MEM) 106 and to a communication unit (COMM) 107. The latter may utilize intrabody galvanic communication (e.g., Z-Comm) via the electrodes 101.a, 101.b, coil-based communication via inductor 108, or radio frequency (e.g., Bluetooth) wireless communication via antenna 109. This permits programming and interrogating the implanted device 2 using an external programmer.

Figure 2:
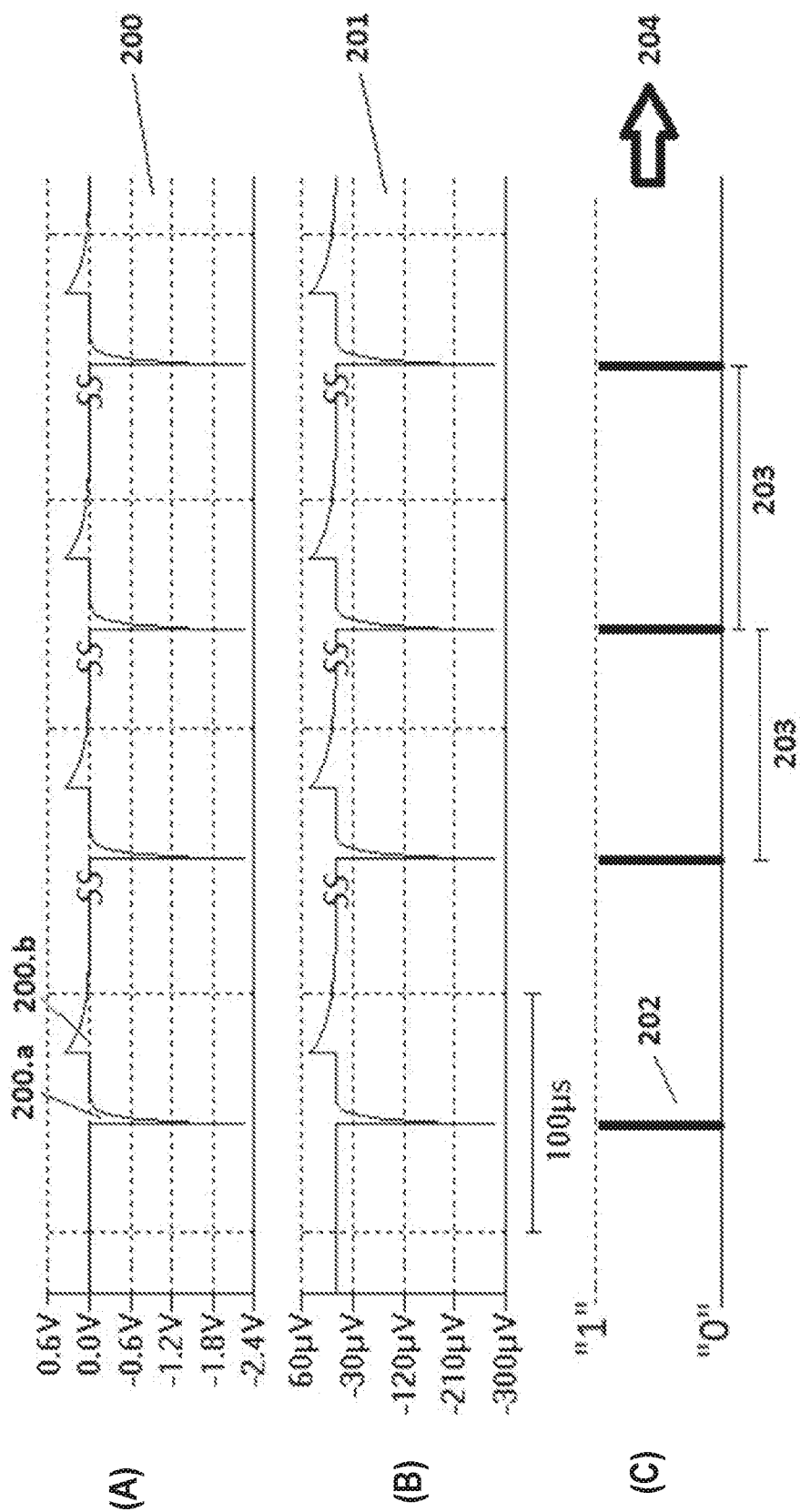
FIG. 2 shows a waveform of the signal as transmitted by the first device (A) and as received by the second device (B), wherein (C) shows a digital signal as transmitted from the first device (A) and received by the second device (B), wherein (C) shows a digital output of the second device generated from the received signal (B)

In a preferred embodiment, each capacitor in the bank 102 has a nominal value of 15 nF. This implies the maximum charge accumulated in each of these capacitors, to be discharged in tissue for transmitting the occurrence of an intrinsic sensed event, can be made sub-threshold to nerve/cardiac stimulation. The preferred pattern of discharges 200 that may start with a sensed intrinsic tissue depolarization is shown in FIG. 2. The same module 100, of at least another (here second) implantable device 3 of the medical system 1, different from the transmitting first device 2, enables a receiver unit 110 connected to its contacts 101.a, 101.b to detect the galvanic-signaled event S (cf. e.g., FIG. 1 left hand side).

As shown in FIG. 2, the trace 200 is the waveform created between electrodes 101.a, 101.b of transmitting module 100 of the first device 2 upon the discharge 200.a of the bank of capacitors 102 in tissue and associated charge balance phases 200.b, when this bank of capacitors 102 is charged to a battery 104 voltage of 2.5 V for example. Given the small value of these capacitors in bank 102, DC blocking capacitor 103 can be in the order of 82 nF which permits fast charge balance phases 200.b in preparation for the next capacitor discharge 200.a. Trace 201, on the other hand, is the attenuated conducted signal received at contacts 101.a, 101.b of the receiver (Rx) unit 110 of module 100 of the second device 3. Trace 202 corresponds to the digital output of the receiver (Rx) unit 110 of the second device 3.

In yet another embodiment, the timing 203 between the high digital outputs 202 permit control unit 105 of the second device 3 to determine an event 204 has been communicated by transmitting module 100 of the first device 2. Further, by shifting the timing 203 between pulses 200.a in the capacitive discharge transmission 200, several bits of information can be communicated beyond the occurrence of event 204, without adding to the energy required. Examples may include transmitting sensed amplitude information, battery status information, etc.

Figure 3A:
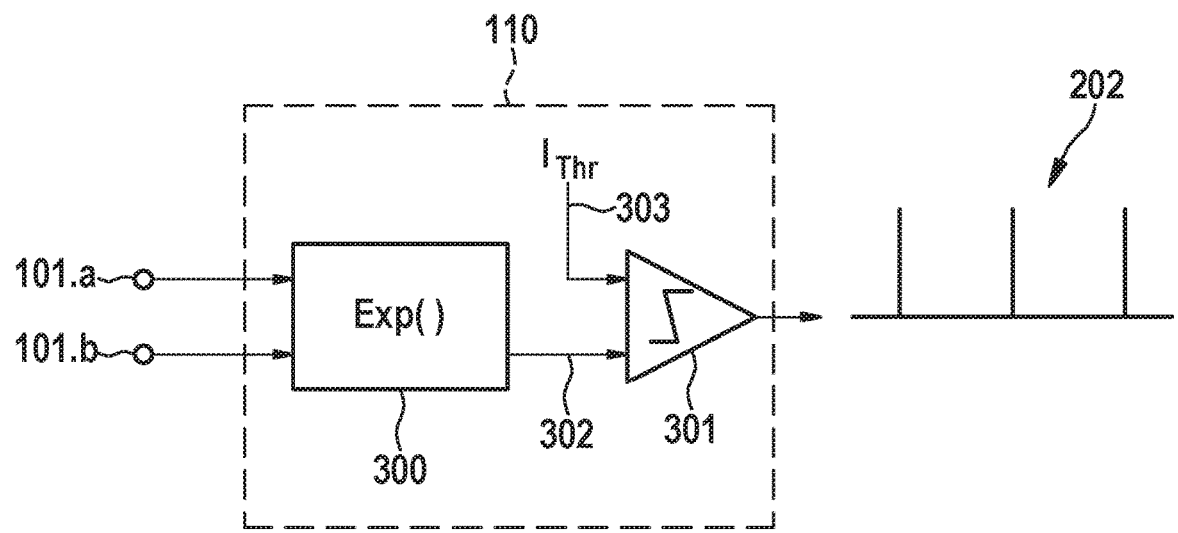
FIGS. 3A-3B show embodiments of a non-linear preprocessor of the first or second device.
Figure 3B:
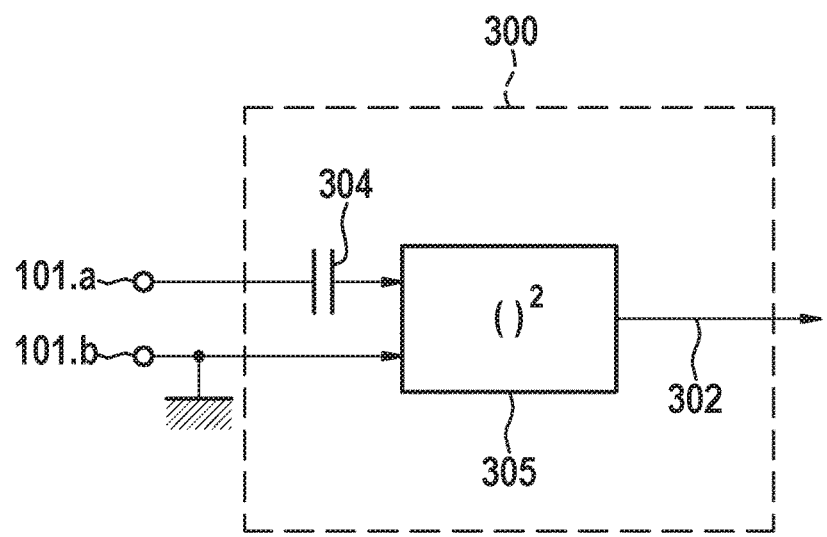

Further, to minimize power consumption of the receiving module 100 of the second device 3, the receiver unit 110 comprises a non-linear pre-processor 300 to extract waveform 200.a, enhancing the difference between these peaks 200.a and the noise level, followed by a current-based comparator 301 as shown in FIGS. 3A-3B. In a preferred embodiment, pre-processor 300 uses the exponential relationship between gate-source voltage and drain current of a MOS transistor operating in weak inversion to convert the waveform 200.a to a current 302 that can be compared to a threshold $I_{Thr}$ 303 (cf. FIG. 3A). In an alternative embodiment, non-linear processor 300 consists of a differentiator (implemented by capacitor 304) and a squaring circuit 305 instead (cf. FIG. 3B). In a preferred embodiment, the total power consumption of the receiver (Rx) unit 110 is lower than 100 nA @ 1.5 V.

Particularly, the galvanic-communication scheme according to the present disclosure permits implementing a medical system 1 with distributed implanted devices 2, 3, for example: i) two leadless pacemakers, one implanted in the right atrium and another one in the right ventricle for implementing the functions of a DDD(R) pacemaker; ii) a leadless pacemaker in communication with a subcutaneous loop recorder with Bluetooth® capabilities; and/or iii) a leadless pacemaker in communication with a subcutaneous implantable cardioverter-defibrillator (ICD).

In other embodiments, the capacitor bank 102 is charged as described, but discharged into a communication element 111 in module 100 of the first device 2, such as a coil or piezoelectric element. The coil 111 will emit a magnetic field which will be detected via a coil 112 in an adjacent receiving device 3, and the piezoelectric element 111 will emit a pressure wave per capacitor discharge which is detectable via a piezoelectric detector 112 in the receiving device 3. In each of these examples, the bank of capacitors (CAPS BANK) 102 is used to charge from the battery 104 and store energy for communication, and communication is facilitated by sequential capacitor discharges to a communication element 111.

Figure 4:
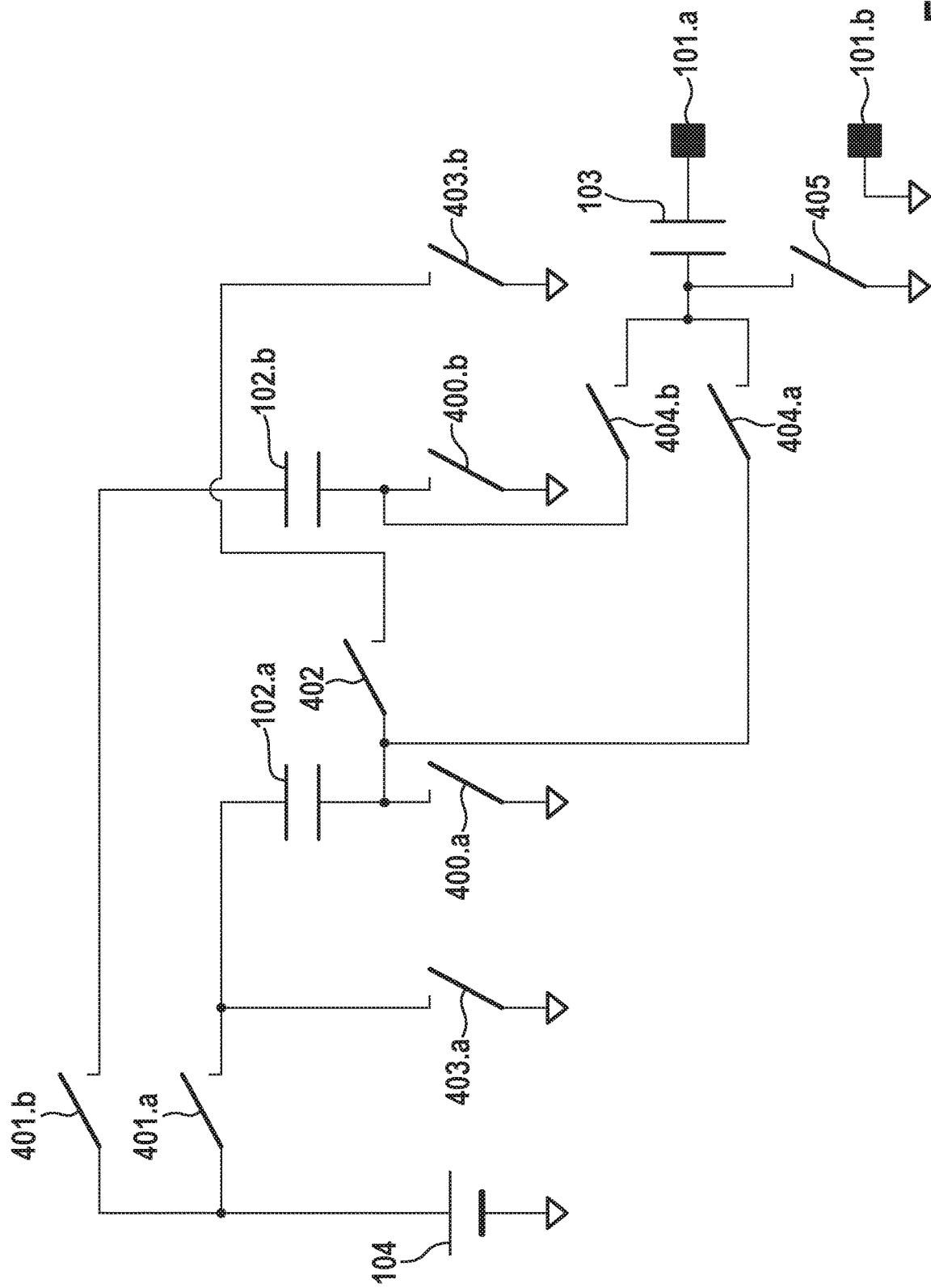
FIG. 4 illustrates some analog switches in the capacitor bank.

FIG. 4 illustrates the analog switches required in the capacitor bank 102 showing two capacitors 102.a and 102.b for simplicity. Analog switches 400, 401 (e.g., transistors) permit charging capacitors 102.a and 102.b to battery voltage 104. By utilizing analog switches 401.a, 402, and 400.b the capacitors 102.a and 102.b can be charged in series to a voltage lower than battery voltage 104. To discharge capacitor 102.a in tissue via electrodes 101.a, 101.b to generate peak 200.a for example, analog switches 403.a, 404.a are closed. Vice versa, to discharge capacitor 102.b, analog switches 403.b and 404.b are closed instead. To perform each charge balancing 202.b, analog switch 205 is closed.

The disclosed intra-body communication scheme is suitable for implementation in reduced-size implantable devices, such as leadless pacemakers and loop recorders, as the bank of capacitors 102 is suited for integrated-passive technology and does not require stepping up the battery voltage.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. An implantable medical system for intra-body communication, comprising:
an implantable first device, wherein the first device comprises a plurality of capacitors and a DC blocking capacitor, and wherein the first device is configured to discharge the plurality of capacitors via the DC blocking capacitor in an encoded sequence to generate a signal.

2. The implantable medical system according to claim 1, wherein a maximum charge accumulated in each of the capacitors of the plurality of capacitors is sub-threshold to nerve stimulation or cardiac stimulation of a patient when discharged in tissue of the patient.

3. The implantable medical system according to claim 1, wherein the capacitors of the plurality of capacitors are configured to be charged to a voltage of a battery of the first device or to a reduced voltage generated from the voltage of the battery of the first device.

4. The implantable medical system according to claim 1, wherein the DC blocking capacitor comprises a capacity in the range from 60 nF to 100 nF, particularly 82 nF.

5. The implantable medical system according to claim 1, wherein the first device further comprises a control unit configured to control the plurality of capacitors, wherein particularly the control unit is configured to control charging and/or discharging of the plurality of capacitors.

6. The implantable medical system according to claim 1, wherein each capacitor of the plurality of capacitors comprises a capacity in the range from 10 nF to 20 nF, particularly 15 nF.

7. The implantable medical system according to claim 1, wherein the first device further comprises two electrodes configured for contacting tissue of a patient when the first device is implanted in the patient, wherein the first device is configured to discharge the plurality of capacitors in the encoded sequence in tissue of the patient via the electrodes to generate the signal.

8. The implantable medical system according to claim 7, wherein the first device is configured to discharge the plurality of capacitors in the encoded sequence such that a waveform is created between the two electrodes of the first device in the tissue of the patient, the waveform comprising a plurality of peaks, wherein the respective peak corresponds to a discharge of a capacitor of the plurality of capacitors, and wherein each peak is followed by a charge balancing phase.

9. The implantable medical system according to claim 1, wherein the system further comprises an implantable second device that is configured to receive the signal and to use the information contained in the signal for performing a function.

10. The implantable medical system according to claim 9, wherein the second device is configured to:
receive the signal via two electrodes of the second device, extract the peaks of the waveform, and convert the respective peak into a corresponding high digital output.

11. The implantable medical system according to claim 10, wherein the second device comprises a control unit, wherein the control unit of the second device is configured to use a timing between the high digital outputs to determine that an event has been communicated by the first device via the signal.

12. The implantable medical system according to claim 11, wherein the first device is configured to shift the timing between the peaks so as to communicate information in addition to the occurrence of event.

13. The implantable medical system according to claim 12, wherein the second device further comprises a non-linear pre-processor which is configured to extract the waveform, and particularly to enhance a difference between the peaks and a noise level.

14. The implantable medical system according to one of the claim 1, wherein the first device is configured to discharge the plurality of capacitors in the encoded sequence into a communication element of the first device.

* * * * *